United States Patent [19]

Yokota

[11] 4,163,320
[45] Aug. 7, 1979

[54] DENTAL OCCLUDING INSTRUMENT

[76] Inventor: Seizo Yokota, 161, Daimyo 1-chome, Chuo-ku, City of Fukuoka, Fukuoka Prefecture, Japan

[21] Appl. No.: 885,216

[22] Filed: Mar. 10, 1978

[51] Int. Cl.² ............................................. A61C 11/00
[52] U.S. Cl. ........................................................ 32/32
[58] Field of Search .................................. 32/32, 19–21

[56] References Cited

U.S. PATENT DOCUMENTS

| | | | |
|---|---|---|---|
| 2,952,914 | 9/1960 | Shackelford | 32/32 |
| 3,359,639 | 12/1967 | Guichet | 32/32 |

FOREIGN PATENT DOCUMENTS 48-37994 6/1973 Japan ............................................. 32/32

*Primary Examiner*—Robert Peshock
*Attorney, Agent, or Firm*—Wenderoth, Lind & Ponack

[57] ABSTRACT

Two slides are slidably fitted into each of two through openings extending in a parallel relationship through a base block and two opposite holders extend perpendicularly from outer end portions of both slides. A threaded rod loosely extends through one of the slides is screw threaded into the other slide to adjust a spacing between the opposite holders. The base block is disposed opposite another identical one so that the holders on the former are aligned with those on the latter and have occluding models for the jaws held by their serrated end portions.

3 Claims, 5 Drawing Figures

DENTAL OCCLUDING INSTRUMENT

BACKGROUND OF THE INVENTION

This invention relates to a dental occluding instrument, and move particularly to a fixing device for controllably fixing a pair of models for the upper and lower jaws to a dental occluding instrument.

Dental occluding instruments are required to accurately reproduce both the anatomical stationariness and physiological functional movements on an instrument other than the oral cavity. This results in the necessity of producing dental occluding instruments with the highest accuracy. Further it is necessary to fixedly secure the models for the jaws to dental occluding instruments in a simple, rapid and accurate manner.

In order to fixedly secure the models for the upper and lower jaws to conventional dental occluding instruments, a bonding agent such as plaster, an adhesive, wax or the like is first poured in between each of the models and a base plate thereof fixed on one supporting surface of the dental occluding instruments. Then, before the bonding agent, for example, plaster, is hardened, either or both of the models for the jaws are or have been moved in any direction or directions to be put in their occlusal positions. Thereafter the gypsum is left to be hardened and to fix the models to the respective base plates. Such conventional dental occluding instruments are disadvantageous in that it is difficult to fix the models for the jaws in their accurate positions because the plaster contracts upon its hardening and considerable time passes until the plaster is hardened. Therefore the job efficiency is difficult to be increased. Also, to re-position either or both of the models for the jaws it is necessary to repeat the process as above-described starting with the first step after the removal of all the bonding agent.

In addition, if the bonding agent is been fully removed from the particular dental occluding instrument, then it is difficult to precisely position new models for the jaws in the same occluding instrument. Further, with dental occluding instruments left with the bonding agent sticking thereto, there is a decrease in accuracy.

Accordingly, it is an object of the present invention to eliminate the disadvantges of the prior art practice as above-described.

It is another object of the present invention to provide a new and improved dental occluding instrument for simply and rapidly holding models for the jaws at their desired positions and for easily re-positioning them.

SUMMARY OF THE INVENTION

The present invention provides a dental occluding instrument comprising a pair of supporting plates disposed in an opposite parallel relationship, a pair of base blocks fixedly secured to the supporting plates to face each other, a plurality of pairs of opposite holding member in the form of rods disposed substantially perpendicularly to each of the base blocks which extend and are aligned with the holding members operatively associated with the other base block, and control means for each pair of the opposite holding members disposed in each of the base blocks to control a spacing formed between the opposite holding member. All of the hold members holding a pair of models for the upper and lower jaws in the occluding state in such a manner that the model for the upper jaw is put in compressive contact with free end portions of the holding members projecting beyond one of the base blocks and the model for the lower jaw is put in compressive contact with the free end portions of the holding members projecting beyond the other base block.

In a preferred embodiment of the present invention each of the base blocks includes a pair of through rectangular openings extending therethrough which are parallel to each other and to the supporting plate. A pair of first and second slides slidably fit into each of the through openings opposite to each other, and the first and second slides including respective outer end portion project from the mating through opening when abutting against each other. A pair of first and second circular holes longitudinally disposed in the first slide are parallel to each other, and the first circular hole extends throughout the length of the first slide. A pair of third and fourth circular holes longitudinally disposed in the second slide are parallel to each other, and the second, third and fourth circular holes are closed at one end located in the outer end portions of the associated slides, the third hole being internally threaded throughout the length thereof. The first and second holes are aligned with the third and fourth holes respectively. Each pair of the opposite holding members is disposed at the closed ends of the second and fourth holes aligned with each other and includes respective portions projecting from the mating slide. The control means includes a threaded rod extending through the first hole and a screw threaded into the third hole, the threaded rod including a portion extending from the first hole and terminating at a head, and a helical spring disposed around the extended portion of the threaded rod between the head and the adjacent end of the first slide. The threaded rod is rotated to move the opposite slides toward and away from each other to control the spacing between the opposite holding members.

BRIEF DESCRIPTION OF THE DRAWING

The present invention will become more readily apparent from the following detailed decription taken in conjunction with the accompanying drawings in which.

DESCRIPTION OF THE PREFERRED EMBODIMENT

Figure 1:
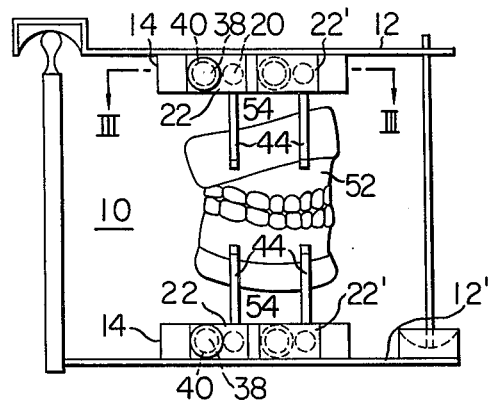
FIG. 1 is a side elevational view of a dental occluding instrument embodying the principles of the present invention.

Referring now of FIG. 1 of the drawing, there is illustrated a dental occluding instrument embodying the principles of the present invention. The arrangement illustrated comprises an arcontype articulator generally designated by the reference numeral 10 and includes a pair of upper and lower supporting plates 12 and 12′ respectively horizontally disposed in opposite relationship with a predetermined spacing therebetween. A pair of square base blocks 14 is fixedly secured in place to the inner opposing surfaces of the supporting plates 12 and 12' in the manner as will be described hereinafter. The base blocks 14 opposite to each other are of the same construction, and one of them, for example, the upper base block 14 as viewed in FIG. 1, is described below.

Figure 2:
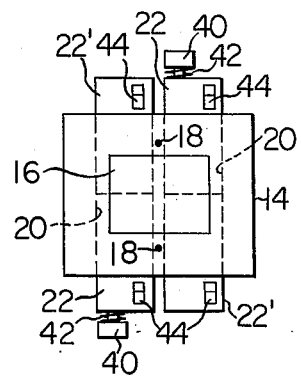
FIG. 2 is a plan view of the fixing device for one of the models for the jaws shown in FIG. 1 with parts omitted.
Figure 4:
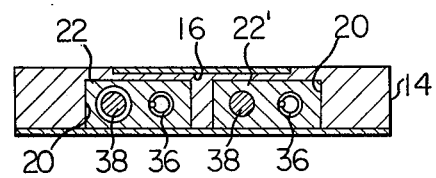
FIG. 4 is a sectional view taken along the line IV—IV of FIG. 3.
Figure 5:
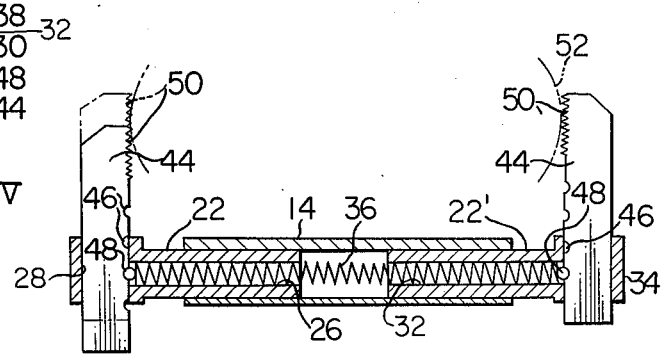
FIG. 5 is a sectional view taken along the line V—V of FIG. 3 with parts illustrated in elevation.

Referring now to FIG. 2, there is illustrated the base block 14 and associated components constructed in accordance with the principles of the present invention. The base block 14 includes a rectangular piece 16 of magnetic sheet centrally disposed on one of the opposite surfaces, and a pair of small holes 18 perpendicularly extending therethrough at the positions where both holes are located on the central axis of the base block 14 and somewhat spaced away from the adjacent sides of the rectangular magnetic piece 16. As best shown in FIG. 4, the rectangular magnetic piece 16 is buried in the upper surface portion as viewed in the same Figure of the base block 14 flush with the upper surface thereof.

As seen in FIG. 2, a pair of rectangular through openings 20 extend through the entire length of the base block 14 along both sides of the central axis which has the holes 18 lying thereon. The openings 20 are parallel to each other and to the upper and lower surfaces of the base block 14. One of those surfaces, in this case, the lower surface as viewed in FIG. 4 is attached to the supporting plate 12. Then a pair of slides 22 and 22' having the same dimensions are slidably fitted into each of the through openings 20, thereby positioning them opposite to each other. The slides have outer end portions projecting from the adjacent lateral surfaces of the base block 14 respectively even when the slides abut against each other. The slide 22 is provided with a first circular bore 24 longitudinally extending the entire length thereof and second circular bore 26 longitudinally extending therethrough parallel to the first bore 24. The bore 26 terminates at a rectangular bore 28 extending through the entire thickness of the outer end portion thereof and is substantially perpendicular to the circular bore 26. Thus, the second hole 26 is closed at one end. The slides 22' include a third circular bore 30 longitudinally extending therethrough and terminating short of the outer end thereof and a fourth circular bore 32 identical to the bore 26 disposed in the slide 22 parallel to the bore 11. The bore 30 is internally threaded throughout its entire length. Like the second bore 26 in the slide 22, the fourth bore 32 in the slide 22' communicates with a rectangular bore 34 disposed in the slide 22 and is identical to the rectangular bore 28 in the slide 22. When the slides 22 and 22' are fitted in opposite relationship into each of the through openings 20, the first bore 24 is longitudinally aligned with third bore 30 while the bores 26 and 32 disposed in the slides 22 and 22' respectively are also longitudinally aligned with each other.

Figure 3:
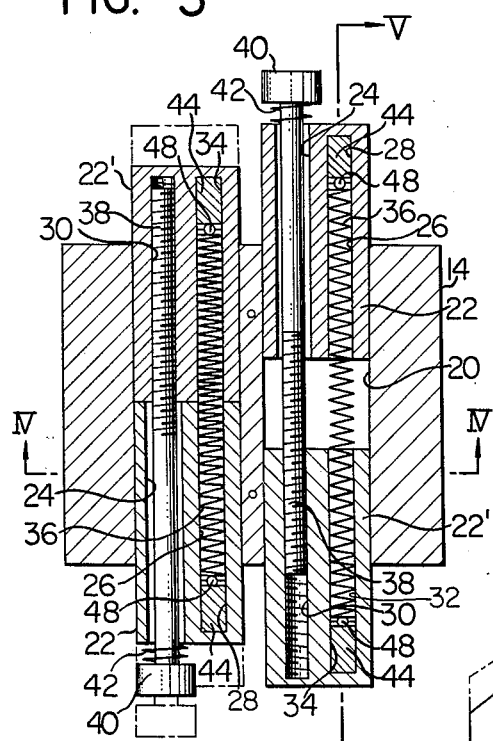
FIG. 3 is a sectional view, partly in plan, of the fixing device taken along the line III—III of FIG. 1.

As seen in FIG. 3, one pair of slides 22 and 22' is slidably fitted into one of the through opening 20 in the base block 14, the slides being opposite to each other with a single helical spring 36 inserted into the opposite aligned bores 26 and 32 disposed in the slides 22 and 22'. Similarly, the other pair of slides 22 and 22' is fitted into the other through opening 20 in the base block 14 with a single helical spring 36 inserted into the opposite aligned bores 26 and 32 disposed in both slides, but the slides 22 and 22' fitted into each of the openings 20 are adjacent to the slides 22 and 22' fitted into the other opening 20 respectively. The slides 22 and 22' fitted into each opening 20 include respective outer end portions projecting from the adjacent ends of the base block 14 and can abut against each other on the middle portion of the opening 20 as shown on the lefthand portion of FIG. 3. Alternatively, both sides 22 and 22' may be spaced away from each other as shown on the righthand portion of FIG. 3.

To this end, a threaded rod 38 with a larger diameter head 40 loosely extends through the circular bore 24 and is screw threaded into the threaded bore 30. When both slides abut against each other, the rod 38 has its threaded portion threaded into the threaded bore 30 throughout its length. Then, a compression spring 42 is disposed around the rod 38 between the head 14 and the adjacent end of the slides 22 or 22'.

Further a pair of rod-shaped holding members 44 complementary in cross section to the rectangular bores 34 in the opposite slides 22 and 22' are fitted into the opposite bores 34 to extend perpendicularly from the slides 22 and 22' so as to permit that portion of each holding member 44 extending from either of the slides 22 and 22' to be manually controlled in length. To this end, each of the holding members 44 is provided on the surface opposite to the other holding member 44 with a plurality of small semicircular notches 46 disposed at equal intervals. The holding member 44 is fitted into the bore 34 so that a selected one of the notches 46 substantially lies on the axis of the bore 26 or 32 and engages a small ball 48 contacting the end of the helical spring 36 to thereby affix the holding member 44 to the associated slide 22 or 22'. It is noted that the holding member 44 projects from that surface of the base block 14 remote from the rectangular magnetic piece 16. It will readily be understood that, by selecting that notch 46 engaging the ball 48, the length of that portion of the holding member 44 projecting from the associated slide 22 or 22' can be manually adjusted in an incremental manner. That is, the holding member is permitted to be notched.

Each pair of opposite rod-shaped holding members 44 are provided on the opposite surfaces of the free end portions thereof with serrations 50 for the purpose as will be apparent hereinafter.

After the rod-shaped holding members 44 have been fixedly secured to each base block 14 in the manner described, both base blocks 14 are mounted in place to the upper and lower supporting plates 12 and 12' of the articulator 10 by fitting positioning pins (not shown) planted on the opposite surfaces of both supporting plates 12 and 12' into the associated positioning holes 18 in the respective base blocks 14 with the magnetic pieces 16 on the base blocks 14 facing each other. Then, a permanent magnet (not shown) is suitably disposed on each of the upper and lower supporting plates 12 and 12' to attract the individual magnetic piece 16 and thereby maintain each of the base blocks 14 fixed in place on the associated supporting plate. At that time, the rod-shaped holding members 44 pendent from the upper base block 14 are vertically aligned with those erected on the lower base block 14 respectively, and it is assumed that all the holding members 44 project identical lengths from the associated base blocks 14 respectively while each pair of opposite slides 22 and 22' fitted into a different one of the through openings 20 abut against each other at the middle point of the associated opening 20.

Under these circumstances, the heads 40 of the threaded rods 38 are successively rotated in a direction to move the opposite slides 22 and 22' away from each other along the associated through openings 20 as shown on the righthand portion of FIG. 3 until holding members form a space sufficient to put a pair of occluding models 52 for the upper and lower jaws at any desired spatial positions therein. After the models 52 have been held at those positions by the serrated end portions of the holding members 44, the heads 40 of the threaded rods 38 are successively rotated in the opposite direction until the serrated end portion of the holding members 44 on the upper base block 14 are in compressive contact with the model for the upper jaw and those on the lower base block 14 are in compressive contact with the model for the lower jaw, thereby carrying the models in their occluding positions. Accordingly, the holding members holding the models 52 leave a space 54 between each model and the adjacent base block 14. Also, the serrated end portions 50 of the holding members 44 are effective for preventing the models 52 from sliding down therealong.

Each pair of opposite slides 22 and 22' receives a force exerted by the associated spring 42 while contacts between the holding members 44 and models 52 for the jaws receive reactions so that each pair of opposite slides are somewhat deflected thereby are fixed in the associated opening 20 that is to say, are prevented from sliding within that opening 20. This maintains the holding members 44 fixed in the associated opening 20 and ensures that the position where the models 52 for the jaws are held remains unchanged.

Since the models 52 for the jaws are generally formed of gypsum and therefore are brittle, any of the holding members 44 may crumble or strip off that portion of the model's surface engaging the same. In the case, that holding member 44 can be forced into the stripped portion of the model surface by means of the action of the associated spring 42 until it is put into compressive contact with the stripped surface portion. Thus, the models 52 are prevented from separating from the holding members 44 and the models 52 are safely held by the holding members without slipping out from the latter.

From the foregoing it is seen that the present invention provides a device for simply and rapidly fixing a pair of models or gypsum for the jaws to an occluding instrument in a precise and durable manner.

While the present invention has been illustrated and described in conjunction with a single preferred embodiment thereof it is to be understood that numerous changes and modification may be resorted to without departing from the spirit and scope of the present invention.

What is claimed is:

1. A dental occluding instrument comprising a pair of supporting plates disposed in opposite parallel relationship, a pair of base blocks fixedly secured to said supporting plate to face each other, a plurality of pairs of opposite holding members in the form of rods disposed substantially perpendicularly to each of said base blocks to extend toward the other base block and be aligned with said holding members operatively associated with the other base block respectively, and control means for each pair of said holding members disposed in each of said base blocks to control a spacing formed between said opposite holding members, all said holding members holding a pair of models for the upper and lower jaws in such a manner that the model for the upper jaw is put in compressive contact with free end portion of said holding members projecting beyond one of said base blocks and the model for the lower jaw is put in compressive contact with free end portions of said holding members projecting beyond the other base block.

2. A dental occluding instrument as claimed in claim 1 wherein each of said base blocks includes a pair of rectangular through openings extending therethrough to be parallel to each other and to said supporting plate, a pair of first and second slides slidably fitted into each of said through openings to be parallel to each other, said first and second slides including respective outer end portions projecting from the mating opening when abutting against each other, a pair of first and second circular holes longitudinally disposed in said first slide to be parallel to each other, said first hole extending throughout the length of said first slide, a pair of third and fourth circular holes longitudinally disposed in said second slide to be parallel to each other, said second, third and fourth holes being closed at one end located in the outer end portions of the associated slides, said third hole being internally threaded throughout the length thereof, said first and second holes being aligned with said third and fourth holes respectively; each pair of said opposite holding members being disposed at said closed ends of said second and fourth holes aligned with each other and including respective portions projecting from the mating slide and wherein said control means includes a threaded rod extending through the first hole and screw threaded into said third hole, said threaded rod including a portion extending from said first hole and terminating at a head, and a helical spring disposed around said extended portion of said threaded rod between said head and the adjacent end of said first slide, whereby said threaded rod is rotatable to move said opposite slides forward and away from each other to control the spacing between said opposite holding members.

3. A dental occluding instrument as claim 2 wherein said opposite slides are provided at said closed ends of said second and third holes with through holes extending therethrough to be perpendicular to said second and fourth holes and each of said holding members is fixedly fitted into said through hold and permitted to be notched.

* * * * *